(12) United States Patent
Caggiano et al.

(10) Patent No.: US 7,425,580 B2
(45) Date of Patent: Sep. 16, 2008

(54) (DIARYL-METHYL)-MALONONITRILES AND THEIR USE AS ESTROGEN RECEPTOR LIGANDS

(75) Inventors: Thomas Joseph Caggiano, Morrisville, PA (US); Antony Aldo Brazzale, Loxanatchee, FL (US)

(73) Assignee: Wyeth, Madison, NJ (US)

( * ) Notice: Subject to any disclaimer, the term of this patent is extended or adjusted under 35 U.S.C. 154(b) by 477 days.

(21) Appl. No.: 11/124,808

(22) Filed: May 9, 2005

(65) Prior Publication Data

US 2006/0014831 A1  Jan. 19, 2006

Related U.S. Application Data

(60) Provisional application No. 60/572,859, filed on May 19, 2004.

(51) Int. Cl.
*A61K 31/135* (2006.01)
*C07C 255/32* (2006.01)

(52) U.S. Cl. .................. 514/648; 558/303; 558/388; 514/579; 514/646

(58) Field of Classification Search ............... 558/303, 558/388, 410; 514/579, 646, 648
See application file for complete search history.

(56) References Cited

U.S. PATENT DOCUMENTS

| 5,789,427 | A | 8/1998 | Chen et al. ................ 514/352 |
| 5,929,117 | A | 7/1999 | Muller et al. ............... 514/576 |
| 2001/0002391 | A1 | 5/2001 | Brand et al. ................ 514/2 |
| 2003/0045726 | A1 | 3/2003 | Muller et al. ............... 546/330 |
| 2003/0087955 | A1 | 5/2003 | Miller et al. ............... 514/453 |

FOREIGN PATENT DOCUMENTS

| EP | 1 018 514 A1 | 7/2000 |
| WO | 96/40137 A1 | 12/1996 |
| WO | 99/65449 A2 | 12/1999 |
| WO | 99/65495 A1 | 12/1999 |
| WO | 00/56706 A1 | 9/2000 |
| WO | 01/00610 A1 | 1/2001 |
| WO | 01/30774 A1 | 5/2001 |
| WO | 01/77055 A2 | 10/2001 |
| WO | 03/051805 A2 | 6/2003 |

OTHER PUBLICATIONS

Latif et al (1974): STN International HCAPLUS database, (Columbus, Ohio), Accession No. 1974:463372.*
Cefalu, W., "The Use of Hormone Replacement Therapy in Postmenopausal Woman with Type 2 Diabetes," *J Womens Health & Gender-based Med.*, 2001, 10(3), 241-255.
Yuan et al., "Reversal of Obesity- and Diet-Induced Insulin Resistance with Salicylates or Targeted Disruption of *Ikkβ*," *Science*, 2001, 293, 1673-7.

Pelletier et al., "Osteoarthritis, an Inflammatory Disease," *Arthr. & Rheum.*, 2001, 44:1237-1247.
Felson, D. T. et al., "The effects of estrogen on osteoarthritis,", *Curr Opinion Rheum*, 1998, 10, 269-272.
Lin, C. C. et. al., "Pulmonary function changes and increased Th-2 cytokine expression and nuclear factor kB activation in the lung after sensitization and allergen challenge in brown Norway rats," *Immunol. Lett.*, 2000, 73, 57-64.
Roth, A. et. al., "Phytoestrogen Kaempferol (3,4' ,5,7-Tetrahydroxyflavone) Protects PC12 and T47D Cells From β-Amyloid-Induced Toxicity," *J. Neurosci. Res.*, 1999, 57, 399-404.
Bauer M. A., Herrmann F., "Interleukin-6 in clinical medicine," *Ann. Hematol.*, 1991, 62, 203-210.
Kurebayashi S. et. al., "Characterization of Mechanisms of Interleukin-6 Gene Repression by Estrogen Receptor," *J. Steroid Biochem. Molec. Biol.*, 1997, 60, 11-17.
Adams, M. R. et al., "Inhibition of Coronary Artery Atherosclerosis by 17-beta Estradiol in Ovariectomized Monkeys," *Arterio.*, 1990, 10(6), 1051-1057.
Sullivan, T. R. et al. "Estrogen Inhibits the Response-to-Injury in a Mouse Carotid Artery Model," *J. Clin. Invst.*, 1995, 96, 2482-8.
Nathan, L. et. al., "Estradiol Inhibits Leukocyte Adhesion and Transendothelial Migration in Rabbits In Vivo," *Circ. Res.*, 1999, 85, 377-385.
Delyani, J. A. et al., "Protection from Myocardial Reperfusion Injury by Acute Administration of 17 β-Estradiol," *J. Molec. Cell. Cardiol.*, 1996, 28, 1001-1008.
Reis et. al., "Estrogen Is Associated With Improved Survival in Aging Women With Congestive Heart Failure: Analysis of the Vesnarinone Studies," *J. Am. Coll. Cardio.*, 2000, 36, 529-33.
Grodstein, F. et. al., "A Prospective, Observational Study of Postmenopausal Hormone Therapy and Primary Prevention of Cardiovascular Disease," *Ann. Int. Med.*, 2000, 133, 933-41.
Alexander et. al., "Initiation of Hormone Replacement Therapy After Acute Myocardial Infarction Is Associated With More Cardiac Events During Follow-Up," *J. Am. Coll. Cardio.*, 2001, 38, 1-7.

(Continued)

*Primary Examiner*—Golam M Shameem
(74) *Attorney, Agent, or Firm*—Pepper Hamilton LLP

(57) ABSTRACT

The present invention concerns compounds of formula:

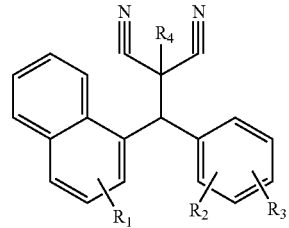

where $R_1$, $R_2$, $R_3$ and $R_4$ are defined in the specification.

14 Claims, No Drawings

OTHER PUBLICATIONS

Grodstein F. et. al., "Postmenopausal Hormone Use and Secondary Prevention of Coronary Events in the Nurses' Health Study," *Ann. Int. Med*, 2001, 135,1-8.

Schonknecht, P. et. al., "Reduced cerebrospinal fluid estradiol levels are associated with increased β-amyloid levels in female patients with Alzheimer's disease," *Neurosci. Lett.*, 2001, 307, 122-124.

Hulley, S. et. al., "Randomized Trial of Estrogen Plus Progestin for Secondary Prevention of Coronary Heart Disease in Postmenopausal Woman," *J. Am. Med. Assoc.*, 1998, 280, 605-13.

Gupte, S. D. et al., "Synthesis of diaryl methylmalonates and analogous compounds," *J Organic Chem*, 1959, 24, 1334-1336.

Y. Sumida, "Functional Polymers. VII. Ethyl 4-Vinyl-α-cyano-β-phenylcinnamate," *Polymer Journal* (1981) 13, 521-536.

W. Lehnert, "Verbesserte Variante Der Knoevenagel-Kondensation MIT TiCl₄/THF/Pyridin(1). Alkyliden- und Arylidenmalonester bei 0—25° C.," *Tetrahedron Lett.* (1970), 54, 4723.

J. Simpson, "New solid phase Knoevenagel catalyst," *Tetrahedron Lett.*, (1999), 40, 7031-7033.

Latif, N., "Naphthalenes. Naphthyl-cyanoalkanoates, -cyanoalcohols and —malonamic acids of Anticipated Broad Spectrum Biological Activity," *Egypt J. Chem* (1974) 17, 879-887.

Latif, N. et al. "Synthesis of Malononitriles of Potential Cystostatic and Pesticidal Activity by Reaction of Grignard Reagents with Ylidenemalononitriles," *J. Chem Soc., Perkin Trans. I*, 1974, 8, 875-879.

Fadda, A. A. et al., "Synthesis of some phenanthrene derivatives structurally related to certain analgesic and antipyretic drugs," *Ind. J. Chem* (1990) 29B, 171-173.

El-Hashash, M. et al., "Some Reactions with Arylidene Malononitrile, Malonic Acid and Malonic Ester," *Pakistan J. Sci. Ind. Res.*, 1977, 20(6), 325-329.

Mizuno et al, "Regioselective Double Vicinal Carbon-Carbon Bond-Forming Reactions of Electron-Deficient Alkenes by Use of Allylic Stannanes and Organoiodo Compounds," *J. Am Chem Soc* 1988 110, 1288-1290.

Yagi, K., "Short Communications. A Simple Fluorometric Assay for Lipoperoxide in Blood Plasma," *Biochemical Medicine* 15: 212-216 (1976).

Shughrue, P. J. et al., "Regulation of Progesterone Receptor Messenger Ribonucleic Acid in the Rat Medial Preoptic Nucleus by Estrogenic and Antiestrogenic Compounds: An in Situ Hybridization Study," *Endocrinology* 138: 5476-5484 (1997).

Merchenthaler, I. et al., The effect of estrogens and antiestrogens in a rat model for hot flush, *Maturitas* 30: 307-316 (1998).

Cuzzocrea, S. et al., "17β-Estradiol Antiinflammatory Activity in Carrageenan-Induced Pleurisy," *Endocrinology* 141: 1455-1463 (2000).

Zaulyanov, L. L. et al., "Glutamate Receptor Requirement for Neuronal Death from Anoxia-Reoxygenation: An in Vitro Model for Assessment of the Neuroprotective Effects of Estrogens," *Cellular & Molecular Neurobiology* 19: 705-718 (1999).

Prokai, L. et al., "Synthesis and Biological Evaluation of 17β-Alkoxyestra-1,3,5(10)-trienes as Potential Neuroprotectants Against Oxidative Stress," *J. Med. Chem.* 44: 110-114 (2001).

A. R. Poole and R. R. A. Coombs, "Rheumatoid-Like Joint Lesions in Rabbits Injected Intravenously with Bovine Serum," *International Archives of Allergy & Applied Inmunology* 54: 97-113 (1977).

Mankin, H. J. et al., "Biochemical and Metabolic Abnormalities in Articular Cartilage from Osteo-Arthritic Human Hips," *Journal of Bone & Joint Surgery*—American vol. 53: 523-537 (1971).

Smirnoff, P. et al., "The Protective Effect of Estrogen Against Chemically Induced Murine Colon Carcinogenesis Is Associated With Decreased CpG Island Methylation and Increased mRNA and Protein Expression of the Colonic Vitamin D Receptor," *Oncology Research* 11: 255-264 (1999).

Dubal, D. B. et al., "Estrogen receptor α, not β, is a critical link in estradiol-mediated protection against brain injury," *PNAS, USA* 98: 1952-1957 (2001).

Dubal, D. B. et al., "Estradiol Modulates bcl-2 in Cerebral Ischemia: A Potential Role for Estrogen Receptors," *J. Neurosci.* 19: 6385-6393 (1999).

Lundeen, S. G. et al., "Rat uterine complement C3 expression as a model for progesterone receptor modulators: characterization of the new progestin trimegestone," *J. Steroid Biochem.* Biol. 78: 137-143 (2001).

Stetson, S. J. et al., "Cardiac Hypertrophy After Transplantation Is Associated With Persistent Expression of Tumor Necrosis Factor- α," *Circulation* 104: 676-681 (2001).

Dietrich, H. et al., "Mouse Model of Transplant Arteriosclerosis," *Arterioscler. Thromb. Vasc. Biol.* 20:343-352 (2000).

Lou, H. et al., "Inhibition of Transplant Coronary Arteriosclerosis in Rabbits by Chronic Estradiol Treatment Is Associated With Abolition of MHC Class II Antigen Expression," *Circulation* 94:3355-3361 (1996).

Karas, R. H. et al., "Effects of Estrogen on the Vascular Injury Response in Estrogen Receptor α,β (Double) Knockout Mice," *Circ. Res.* 89:534-539 (2001).

Cercek, B. et al., "Nuclear factor-κB Activity and arterial response to balloon injury," *Atherosclerosis* 131:59-66 (1997).

Izumi, T. et al., "Blockade of the natriuretic peptide receptor guanylyl cyclase-A inhibits NF-κB activation and alleviates myocardial ischemia/reperfusion injury," *J. Clin. Invest.* 108:203-213 (2001).

Chandrasekar, B. et al. "Ischemia-Reperfusion of Rat Myocardium Activates Nuclear Factor- κB and Induces Neutrophil Infiltration Via Lipopolysaccharide-Induced CXC Chemokine," *Circulation* 103:2296-2302 (2001).

Yokoseki, O. et al., "*cis* Element Decoy Against Nuclear Factor- κB Attenuates Development of Experimental Autoimmune Myocarditis in Rats," *Circ. Res.* 89:899-906 (2001).

Wallen, W. J. et al., "Gender-Differences in Myocardial Adaptation to Afterload in Normotensive and Hypertensive Rats," *Hypertension* 36:774-779 (2000).

Sommer, R. et al., "Synthesen mit *N*-Trialkylstannyl-ketenimen," *Liebigs Ann. Chem.*, 1968, 11-23.

Matsumoto, N. et al., "Synthesis of NF-kB Activation Inhibitors Derived from Epoxyquinomicin C," *Bioorganic & Medicinal Chemistry Letters*, 2000, 10, 865-869.

Jones, G. *Organic Reactions*, 1967, 15, Ch. 2, pp. 204-236 and 357-373.

Hart, H et al., "Synthesis and NMR Spectra of 3-aryl-1,1,2,2-tetracyanocyclopropanes," *Tetrahedron*, 1969, 25, 3869-3877.

Silver, R. F. et al., "Synthesis and chemical reactions of some conjugated heteroenoid compounds," *Can. J. Chem.*, 1967, 45 1001-1006.

Kadokami, T. et al., "Anti-Tumor Necrosis Factor-α Antibody Limits Heart Failure in a Transgenic Model," *Circulation*, 2001, 104, 1094-1097.

Lum, R.T. et al., *Biochem Pharmacol.*, 1998, 55, 1391-1397.

Kohler, E. P. et al., "The Reaction between Unsaturated Compounds and Organic Magnesium Compounds," *Am. Chem. J.*, 1905, 33, 333-356.

Fosse, R., "New reactions of some hydrols," *Bull. Soc. Chim. Fr.*, 1906, 35, 1016-1017.

Sturz, H. G. et al., "Some Substituted Benzalmalononitriles," *JACS*, 1949, 2949.

\* cited by examiner

(DIARYL-METHYL)-MALONONITRILES AND THEIR USE AS ESTROGEN RECEPTOR LIGANDS

CROSS-REFERENCE TO RELATED APPLICATIONS

The present application claims benefit to U.S. Provisional Application Ser. No. 60/572,859, filed May 19, 2004, which is incorporated herein by reference in its entirety.

FIELD OF THE INVENTION

This invention relates to (diaryl-methyl)-malononitriles compounds, and their use as estrogen receptor ligands.

BACKGROUND OF THE INVENTION

The ability of ligands for the estrogen receptor to inhibit inflammatory gene expression (causing a reduction of cytokines, chemokines, adhesion molecules and inflammatory enzymes) is believed to provide a means to treat the inflammatory component of diseases such as atherosclerosis, myocardial infarction (MI), congestive heart failure (CHF), inflammatory bowel disease and arthritis. Other potential therapeutic indications for these type of molecules include type II diabetes (Cefalu, *J. Womens Health & Gender-based Med.*, 2001, 10, 241 & Yuan et al., *Science*, 2001, 293, 1673), osteoarthritis (Pelletier et al., *Arthr. & Rheum.*, 2001, 44:1237 and Felson et al., *Curr Opinion Rheum*, 1998, 10, 269) asthma (Chin-Chi Lin et. al., *Immunol. Lett.*, 2000, 73, 57). Alzheiemer's disease (Roth, A. et al., *J. Neuosci. Res.*, 1999, 57, 399) and autoimmune diseases such as multiple sclerosis and rheumatiod arthritis.

A common component of these chronic inflammatory conditions is suspected to be infiltration of polymorphonuclear leukocytes and monocyltes into the site of damage through increased expression of cytokines and adhesion molecules responsible for their recruitment. Overproduction of the cytokine interleukin (IL-6) has been associated with states of chronic inflammation (Bauer M. A. Herrmann F., *Ann. Hermatol.*, 1991, 62, 203). Synthesis of the IL-6 gene is induced by the transcription factor nuclear factor κB (NF-κB). Interference at this step in the inflammatory process is believed to effectively regulate the uncontrolled proliferative process that occurs in these chronic conditions.

In endothelial cells, 17β-estradiol (E2) inhibits IL-1β induced NF-κB reporter activity and IL-6 expression in an estrogen receptor (ER)-dependent fashion (Kurebayashi S. et. al., *J. Steroid Biochem. Molec. Biol.*, 1997, 60, 11). This has been said to correlate with anti-inflammatory action of E2 in vivo as confirmed in different animal models of inflammation. In models of atherosclerosis, E2 was shown to protect endothelial cell integrity and function, and to reduce leukocyte adhesion and intimal accumulation (Adams, M. R et al., *Arterio.*, 1990, 1051, Sullivan, T. R. et al., *J. Clin. Invst.* 1995, 96, 2482, Nathan, L. et. al., *Circ. Res.*, 1999, 85, 377). Similar effects of estrogen on the vascular wall have also been demonstrated in animal models of myocardial infarction (Delyani, J. A. et al., *J Molec. Cell. Cardiol.*, 1996, 28, 1001) and congestive heart failure. Clinically, estrogen replacement therapy (ERT) has been demonstrated to reduce the risk of mortality in patients with both CHF (Reis et. al., *J. Am. Coll. Cardio.*, 2000, 36, 529) and MI (Grodstein, F. et. al., *Ann. Int. Med.*, 2000, 133, 933, Alexander et. al., *J. Am. Coll. Cardio.*, 2001, 38, 1 and Grodstein F. et. al., *Ann. Int. Med*, 2001, 135, 1). In ERT, clinical studies demonstrated an influence of E2 on the decrease in the production of β-amyloid 1-42 (Aβ42), a peptide central for the formation of senile plaques in Alzheimer's disease (Schonknecht. P. et. al., *Neurosci. Lett.*, 2001, 307, 122).

17-β-Estradiol, however, also strongly stimulates creatine kinase expression. Thus, in ERT some potential unwanted side effects, such as an increase risk of cardiovascular events in the first year of use, have been demonstrated (Hulley, S. et. al., *J Am. Med. Assoc.*, 1998, 280, 605) as well as proliferative effects on uterine and breast tissue.

SUMMARY OF THE INVENTION

The present invention relates to compounds that are able to serve as ligands for the estrogen receptor. Preferred compounds of this type are (diaryl-methyl)-malononitriles. In certain embodiments, such compounds are of formula:

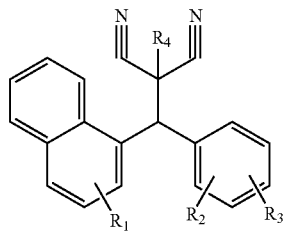

wherein
$R_1$, $R_2$, and $R_3$ are each independently, hydrogen, halogen, alkyl, cycloalkyl, alkoxy, nitro, cyano, alkylthio, $CF_3$, $OCF_3$ or OH; and
$R_4$ is hydrogen, alkyl, alkenyl, arylalkyl, cycloalkyl methyl, or heteroaryl alkyl;
provided that at least one of $R_1$, $R_2$, $R_3$, and $R_4$ is other than H;

and pharmaceutically acceptable salts, hydrates and solvates thereof.

In another aspect, the invention is drawn to pharmaceutical compositions that comprise one or more estrogen receptor ligands and a pharmaceutically acceptable carrier.

In yet other aspects, the invention concerns methods of treating or inhibiting chronic inflammatory disease in a mammal in need thereof, which comprise administering to said mammal an effective amount of a compound of the invention.

Such diseases include rheumatoid arthritis, spondyloarthropathies, osteoarthritis, psoriatic arthritis, juvenile arthritis, inflammatory bowel disease, Crohn's disease, ulcerative colitis, indeterminate colitis, psoriasis, asthma and chronic obstructive pulmonary disease.

The invention is also directed to methods of treating or inhibiting stroke, ischemia, or reperfusion injury in a mammal in need thereof, which comprise administering to said mammal an effective amount of a compound of the invention. In other embodiments, the invention concerns methods of lowering cholesterol, triglvcerides. Lp(a). and LDL levels; inhibiting or treating hypercholesteremia, hyperlipidemia, cardiovascular disease, atherosclerosis, acute coronary syndrome, peripheral vascular disease, restenosis, or vasospasm in a mammal.

In yet other aspects, the compounds of the invention can be used for treating or inhibiting Alzheimer's disease, cognitive decline, senile dementia, or type II diabetes in a mammal.

DETAILED DESCRIPTION OF THE INVENTION

Preferred compounds of the present invention are those that block interleukin-1β (IL-1β) induced nuclear factor κB (NF-κB) luciferase reporter activity or interleukin-6 (IL-6) expression in an ER dependent fashion in human endothelial cells. Compounds useful in the instant invention show preferably little or no proliferative effects on uterine and breast tissue that is associated with estrogen in vivo. A lack of estrogen side effects can be confirmed in vitro by the lack of expression of creatine kinase (CK), a classic estrogen responsive gene. The compounds described herein are expected to prove useful for the treatment and prevention of chronic inflammatory diseases without stimulating uterine and breast cell proliferation as found with classic estrogens.

Compounds of the present invention include (diarlyl-methyl)-malonitriles. In some aspects, the compounds may be represented by the formula:

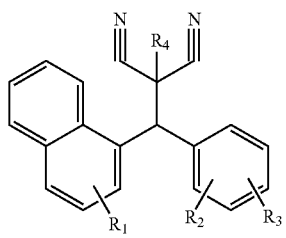

wherein:
$R_1$, $R_2$, and $R_3$ are each independently, hydrogen, halogen, alkyl, cycloalkyl, alkoxy, nitro, cyano, alkylthio, $CF_3$, $OCF_3$ or OH; and $R_4$ is hydrogen, alkyl, alkenyl, arylalkyl, cycloalkyl methyl, or heteroaryl alkyl;

provided that at least one of $R_1$, $R_2$, $R_3$, and $R_4$ is other than H, and pharmaceutically acceptable salts, hydrates and solvates thereof.

In certain compounds, $R_4$ preferably is H. In others, $R_4$ is alkyl, alkenyl, arylalkyl, cycloalkyl methyl, or heteroaryl alkyl.

In some embodiments, at least one of $R_1$, $R_2$, and $R_3$ is halogen, alkyl, cycloalkyl, alkoxy, nitro, cyano, alkylthio, $CF_3$, $OCF_3$ or OH.

$R_1$ and $R_2$ preferalby are each, independently, hydrogen, halogen, alkyl, alkoxy, cyano, $CF_3$ or OH in some compositions. In certain of these compositions, $R_1$ and $R_2$ are the same. In other compositions, $R_3$ prefrably is hydrogen, alkyl, alkenyl, alkylaryl, or heteroaryl methyl. In certain embodiments, $R_1$ and $R_2$ are each, independently, hydrogen, halogen, alkyl, or alkoxy. In still other embodiments, $R_3$, is alkyl, allyl, benzyl.

In certain preferred compounds, $R_1$ and $R_2$ are each H and $R_3$ is halogen, alkyl, alkoxy, cyano, $CF_3$ or OH. In other compounds, $R_1$ and $R_2$ are each H and $R_3$ is halogen, alkyl, or alkoxy. In certain of these compounds, $R_4$ is H. In yet other compounds, $R_3$ is methyl or methoxy Representitive compounds of this invention include:
2-[(2-methoxyphenyl)(1-naphthyl)methyl]malononitrile,
2-[(3-methoxyphenyl)(1-naphthyl)methyl]malononitrile,
2-[(2-methylphenyl)(1-naphthyl)methyl]malononitrile,
2-[(4-methylphenyl)(1-naphthyl)methyl]malononitrile,
2-[(4-methoxyphenyl)(1-naphthyl)methyl]malononitrile,
2-[(2-methoxyphenyl)(1-naphthyl)methyl]-2-methylmalononitrile, and
2-[di(1-naphthyl)methyl]malononitrile.

The invention is also directed to all or any of its stereoisomers and pharmaceutically acceptable salts of the compounds described herein. Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1-6 carbon atoms or dialkylammonium salts containing 1-6 carbon atoms in each alkyl group, and trialkylammonium salts containing 1-6 carbon atoms in each alkyl group, when a compound of this invention contains an acidic moiety.

The term "alkyl", unless otherwise stated, refers to either a ($C_1$-$C_6$) straight chain or ($C_3$-$C_6$) branched-chain monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like.

The term "alkenyl", unless otherwise stated, refers to either a ($C_2$-$C_6$) straight chain or ($C_3$-$C_6$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like.

The term "cycloalkyl", unless otherwise stated, refers to a monocyclic, bicyclic, tricyclic, fused, bridged, or spiro monovalent saturated hydrocarbon moiety of 3-10 carbon atoms, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

The terms "halogen", employed alone or in combination with other terms, is defined herein as, unless otherwise stated, a fluorine, chlorine, bromine, or iodine atom.

The term "aryl", employed alone or in combination with other terms, is defined herein as, unless otherwise stated, an aromatic carbocyclic moiety of up to 20 carbon atoms, 6-20 carabon atoms in some embodiments, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphtenyl, acenaphthylenyl, and the like.

The term "arylalkyl", as used herein refers to the group —R—Ar where Ar is aryl and R is alkyl. Examples of arylalkyl moieties include, but are not limited to, chemical groups such as benzyl, 1-phenylethyl, 2-phenylethyl, diphenylmethyl 3-phenylpropyl, 2-phenylpropyl, fluorenylmethyl, and homologs, isomers, and the like.

The term "heteroaryl", unless otherwise stated, refers to an aromatic heterocyclic ring system, which may be a single ring (monocyclic) or multiple rings (bicyclic, up to three rings) fused together or linked covalently. In some embodiments, heteroaryl groups have 4-20 carbon atoms. The rings may contain from one to four hetero atoms selected from nitrogen (N), oxygen (O), or sulfur (S), wherein the nitrogen or sulfur atom(s) are optionally oxidized, or the nitrogen atom(s) are optionally quarternized. Any suitable ring position of the heteroaryl moiety may be covalently linked to the defined chemical structure. In some embodiments, the heteroaryl group may be an aromatic 5-membered to 7-membered carbon-containing monocyclic ring having one to two heteroatoms which independently may be nitrogen, oxygen or sulfur. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole, 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like.

Heteroaryl chemical groups, as herein before defined, are also optionally saturated or partial saturated heterocyclic rings. Examples of saturated or partially saturated heteroaryl moieties include, but are not limited to, chemical groups such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

The term "heteroarylalkyl" refers to the group —R-heteroaryl where R is alkyl.

The term "alkoxy", unless otherwise stated, refers to either a $(C_1-C_6)$ straight chain or $(C_3-C_6)$ branched-chain hydrocarbon covalently bonded to an oxygen atom. Examples of alkoxy moieties include, but are not limited to, chemical groups such as methoxy, ethoxy, isopropoxy, sec-butoxy, tert-butoxy, decanoxy, and homologs, isomers, and the like.

The term "alkylthio", unless otherwise stated, refers to either a $(C_1-C_6)$ straight chain or $(C_3-C_6)$ branched-chain hydrocarbon covalently bonded to a sulfur atom. Examples of alkylthio moieties include, but are not limited to, chemical groups such as methylthio, ethylthio, isopropylthio, sec-butylthio, tert-butylthio, and homologs, isomers, and the like.

Each of the above terms (e.g., alkyl, aryl, heteroaryl) is meant to include unsubstituted, monosubstituted, and polysubstituted forms of the indicated radical or moiety. Substituents for each type of moiety are provided below.

Substituents for alkyl, alkenyl, cycloalkyl, alkylene, the alkyl portion of arylalkyl and heteroarylalkyl, saturated or partially saturated heterocyclic rings, and acyl moieties include —R', OR', =O, =NR', =N—OR', —NR'R", —SR', halogen —OC(O)R', —CO$_2$R', —C(O)NR'R", —OC(O)NR'R", —NR"C(O)R', —NR"CO$_2$R', —NR'C(O)NR'R", —NH—C(NH$_2$)=NH, —NR'C(NH$_2$)=NH, —NH—C(NH$_2$)=NR', —S(O)R', —S(O)$_2$R', —S(O)$_2$NR'R", cyano, and nitro, where R' and R" each, independently, are hydrogen, unsubstituted $(C_1-C_6)$alkyl, unsubstituted $(C_3-C_7)$cycloalkyl, aryl, aryl-$(C_1-C_3)$alkyl, aryloxy-$(C_1-C_3)$alkyl, arylthio-$(C_1-C_3)$alkyl, heteroaryl, heteroaryl-$(C_1-C_3)$alkyl, heteroaryloxy-$(C_1-C_3)$alkyl, or heteroarylthio-$(C_1-C_3)$alkyl groups, or or optionally taken together (when R' and R" are not hydrogen) to form a ring.

The aryl or heteroaryl moieties, may be optionally mono-, di- or tri-substituted with substituents. Representitive substitutents include —R', —OR', —SR', —C(O)R', —CO$_2$R', -alkoxyalkyl, alkoxyalkyloxy, cyano, halogen, nitro, trifluoromethyl, trifluoromethoxy, —NR'R", alkylaminoalkyl, dialkylaminoalkyl, hydroxyalkyl, —S(O)R', —S(O)$_2$R', —SO$_3$R', —S(O)$_2$NR'R", —CO$_2$R', and C(O)NR'R", —OC(O)NR'R", —NR"C(O)R', —NR"CO$_2$R', —NR'C(O)NR'R", —NH—C(NH$_2$)=NH, —NR'C(NH$_2$)=NH, —NH—C(NH$_2$)=NR', —S(O)R', and —S(O)$_2$R', where R' and R" each, independently, are hydrogen, $(C_1-C_6)$alkyl, $(C_1-C_7)$cycloalkyl, aryl, aryl-$(C_1-C_3)$alkyl, aryloxy-$(C_1-C_3)$alkyl, arylthio-$(C_1-C_3)$alkyl, heteroaryl, heteroaryl-$(C_1-C_3)$alkyl, heteroaryloxy-$(C_1-C_3)$alkyl, or heteroarylthio-$(C_1-C_3)$alkyl groups, or optionally taken together (when R' and R" are not hydrogen) to form a ring.

The compounds of the present invention may contain an asymmetric atom, and some of the compounds may contain one or more asymmetric atoms or centers, which may thus give rise to optical isomers and diastereomers.

One synthetic approach to compounds of the present invention is described in Scheme 1.

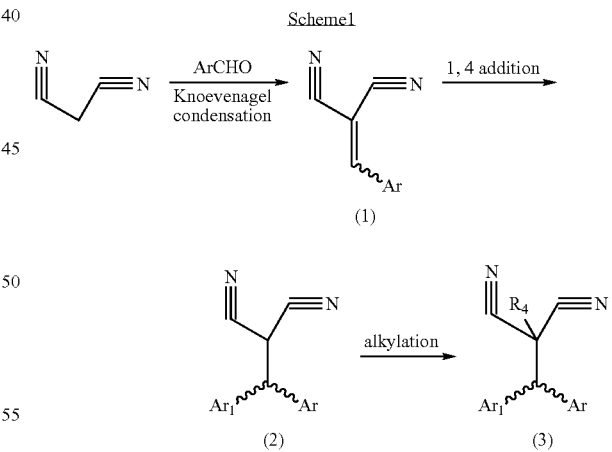

Scheme 1

The starting materials used herein are commercially available or are prepared by methods known to one skilled in the art. These methods can be found in standard references such as "*Handbook of Reagents for Organic Synthesis*" Volumes 1-4 (John Wiley & Sons, Chichester, UK, 1999) and Organic Reactions, Volumes 1-55 (John Wiley & Sons, NY).

Condensation of a malonitrile with an optionally substituted aromatic or heteroaromatic aldehyde in the presence of a catalyst provides the intermediate (1) as shown in Scheme 1. The catalyst can be a salt derived from an amine and a carboxylic acid (e.g. ammonium formate or an amino acid such as alanine, (G. Jones, *Organic Reactions,* 1967 15, 204; Y. Sumida, *Polymer Journal,* 1981 13, 521), a Lewis acid such as titanium tetrachloride in pyridine (W. Lehnert, *Tetrahedron Lett.,* 1970, 54, 4723), or an amine immobilized on a resin (J. Simpson, *Tetrahedron Lett.* 1999, 40, 7031). Recently, ionic liquids have also found use as media for base-catalyzed Knoevenagel reactions. Michael addition of an aryl Grignard or lithium/copper (e.g. Gilman type) reagent (N. Laitif, *J. Chem. Soc.,* 1974, 875; Gupte, *J. Org. Chem.,* 1959, 24, 1334) to the condensation product provided the substituted malononitrile (2). Alkylation of the anion of (2) with an alkyl halide or sulfonate (A. A. Fadda, *Ind. J. Chem.* 1990, 29B, 171) provides the desired bisnitrile (3).

An alternative synthesis of Intermediate 2 (wherein $Ar_1$=naphthyl and Ar=phenyl) involves the synthesis of a diaryl methyl halide (or equivalent) and its use in a sequential alkylation of malononitrile as shown in Scheme 2

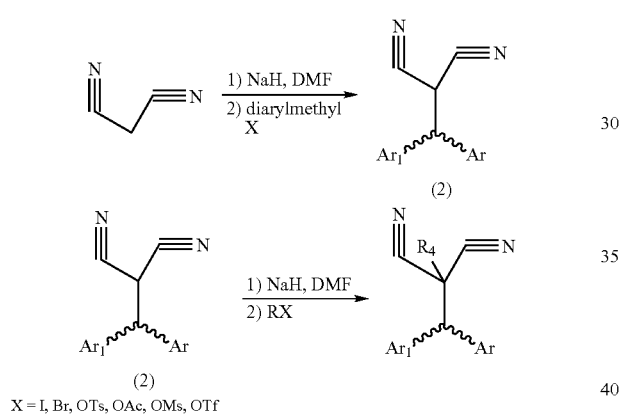

The intermediate diarylmethyl-X in Scheme 2 can be obtained as shown in Scheme 3. The alcohol (3) is converted into a leaving group using methods known to one skilled in the art (e.g. $Ph_3P/CCl_4$, $Ph_3P/CBr_4$, methyltriphenoxyphosphonium iodide, TsCl/Pyr, MsCl/TEA, $Ac_2O/Pyr$).

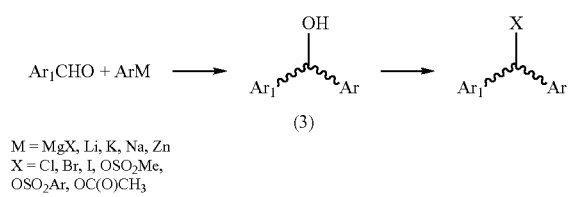

An alternative synthesis of the compounds in which $R_4$ is allyl or benzyl involves the synthesis of a 2-benzhydrylidenemalononitrile using methods known to one skilled in the art (e.g. Knoevenagel reaction) and subsequent addition of an allyl (or benzyl) stannane under the conditions of Mizuno et al (*J. Am Chem Soc* 1988 110, 1288) as shown in Scheme 4.

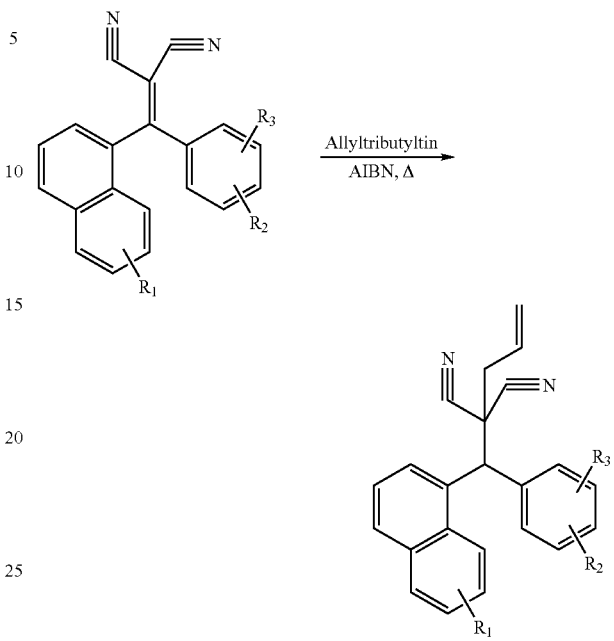

EXAMPLES

Example 1

2-[(2-Methoxyphenyl)(1-naphthyl)methyl]malononitrile

A flask was charged with (1-naphthalenylmethylene)-propanedinitrile (408 mg, 2 mmol) and 10 mL anhydrous tetrahydrofuran. To this stirred solution was added, at room temperature, 2-methoxy phenyl magnesium bromide (2.4 mL, 2.4 mmol, 1 M in tetrahydrofuran). The reaction was stirred 1.5 hours, after which it was quenched with 1 N hydrochloric acid and taken up in ethyl acetate. The organic layer was washed with saturated aqueous sodium bicarbonate, brine, dried over magnesium sulfate, filtered, and evaporated to dryness. Following purification on silica (20% ethyl acetate/hexanes) 551 mg product was isolated as an off white foam.

$^1$H NMR 400 MHz (DMSO-$d_6$): δ 8.14 (d, 1H, J=8.05 Hz), 7.93 (m, 2H), 7.74 (d, 1H. J=7.32 Hz), 7.60 (d, 1H, J=8.05 Hz), 7.53 (m, 2H), 7.27 (t, 1H, J=7.85 Hz), 7.21 (dd, 1H, J=7.81, 1.71 Hz),7.09 (d, 1H, J=7.56 Hz), 6.89 (t, 1H, J=7.75 Hz), 6.02 (d, 1H, J=10.25), 5.97 (d, 1H, J=10.49),3.89 (s, 3H). MS (APCI) m/z 311 [M−H]$^-$; Anal. calcd for $C_{21}H_{16}N_2O$: C, 80.75; H, 5.16 N, 8.97. Found: C, 80.37; H, 5.05 N, 8.70.

Example 2

2-Naphthalen-1-ylmethylene-malononitrile

1-Naphthaldehyde (20 g, 128 mmol), malononitrile (10.15g, 153.7 mmol), piperidine (5.45 g, 64 mmol), 150 mL ethanol, and 100 mL toluene were combined in a flask equipped with a stirbar and refluxed with removal of water for 4 hours, after which the reaction was cooled and taken in up in ethyl acetate. The organic layer was washed with 0.1 N hydrochloric acid, saturated sodium bicarbonate, brine, dried over magnesium sulfate, filtered, evaporated to dryness. The residue was recrystallized from ethyl acetate to yield 8.80 g product as a crystalline solid, mp 165-167° C.;

$^1$H NMR 400 MHz (DMSO-$d_6$): δ 9.36 (s, 1H), 8.25 (m, 2H), 8.17 (d, 1H, J=7.3 Hz), 8.06 (d, 1H, J=7.4 Hz), 7.68 (m, 3H) MS (EI) m/z (M)$^+$ (204) Anal. calcd for $C_{14}H_8N_2$.0.1 mol $H_2O$: C, 81.62; H, 4.01 N, 13.60. Found: C, 81.76; H, 3.76 N, 13.75.

Example 3

2-[(3-Methoxyphenyl)(1-naphthyl)methyl]malononitrile

A flask was charged with (1-naphthalenylmethylene)-propanedinitrile from Example 3 (408 mg, 2 mmol) and 10 mL anhydrous tetrahydrofuran. To this stirred solution was added, at room temperature, 3-methoxy phenyl magnesium bromide (2.4 mL, 2.4 mmol, 1 M in tetrahydrofuran). The reaction was stirred 1.5 hours, after which it was quenched with 1 N hydrochloric acid and taken up in ethyl acetate. The organic layer was washed with saturated aqueous sodium bicarbonate, brine, dried over magnesium sulfate, filtered, and evaporated to dryness. Following purification on silica (20% ethyl acetate/hexanes) 401 mg product was isolated as an off white foam.

$^1$H NMR 400 MHz (DMSO-$d_6$): δ 8.30 (d, 1H, J=8.29 Hz), 7.94 (m, 2H), 7.80 (d, 1H, J=7.32 Hz), 7.62 (t, 1H, J=8.0 Hz), 7.54 (m, 2H), 7.25 (t, 1H, J=8.0 Hz), 7.09 (t, 1H, J=1.95 Hz), 7.04 (d, 1H, J=7.08 Hz), 6.83 (dd, 1H, J=8.30 Hz, 0.73 Hz), 6.11 (d, 1H. J=10.49 Hz), 5.87 (d, 1H, J=10.49 Hz), 3.69 (s, 3H); MS (EI) m/z, 312 (M)$^+$; Anal. calcd for $C_{21}H_{16}N_2O$.0.3 mol $H_2O$ C, 79.37 H, 5.27 N, 8.82. Found: C, 79.32 H, 5.14 N, 8.62.

Example 4

2-[(2-Methylphenyl)(1-naphthyl)methyl]malononitrile

A flask was charged with (1-naphthalenylmethylene)-propanedinitrile of Example 3 (408 mg, 2 mmol) and 10 mL anhydrous tetrahydrofuran. To this stirred solution was added, at room temperature, ortho-tolyl magnesium bromide (1.2 mL, 2.4 mmol, 2 M in tetrahydrofuran). The reaction was stirred 1.5 hours, after which it was quenched with 1 N hydrochloric acid and taken up in ethyl acetate. The organic layer was washed with saturated aqueous sodium bicarbonate, brine, dried over magnesium sulfate, filtered, and evaporated to dryness. Following purification on silica (20% ethyl acetate/hexanes) 455 mg product was isolated as an off white foam.

$^1$H NMR 400 MHz (DMSO-$d_6$): δ 8.38 (d, 1H, J=8.54 Hz), 7.96 (d, 1H, J=8.05 Hz), 7.91 (d, 1H, J=8.05 Hz), 7.60 (m, 1H), 7.54 (m, 2H), 7.46 (m, 2H), 7.24 (m, 1H), 7.20 (m, 2H), 6.04 (d, 1H, J=9.76 Hz), 5.95 (d, 1H, J=9.76 Hz), 2.30 (s, 3H); MS (APCI) m/z 295 [M−H]$^−$; Anal. calcd for $C_{21}H_{16}N_2$: C, 85.11; H, 5.44 N, 9.45. Found: C, 84.81; H, 5.30 N, 9.43.

Example 5

2-[(4-Methylphenyl)(1-naphthyl)methyl]malononitrile

A flask was charged with (1-naphthalenylmethylene)-propanedinitrile of Example 3 (408 mg, 2 mmol) and 10 mL anhydrous tetrahydrofuran. To this stirred solution was added, at room temperature, 4-methylphenyl magnesium bromide (2.4 mL, 2.4 mmol, 1 M in tetrahydrofuran). The reaction was stirred 1.5 hours, after which it was quenched with 1 N hydrochloric acid and taken up in ethyl acetate. The organic layer was washed with saturated aqueous sodium bicarbonate, brine, dried over magnesium sulfate, filtered, and evaporated to dryness. Following purification on silica (15% ethyl acetate/hexanes) 116 mg product was isolated as an off white foam.

$^1$H NMR 400 MHz (DMSO-$d_6$): δ 8.25 (d, 1H, J=7.81 Hz), 7.92 (m, 2H), 7.78 (d, 1H, J=7.32 Hz), 7.61 (t, 1H, J=7.44 Hz), 7.52 (m, 2H), 7.37 (d, 2H, J=7.56 Hz), 7.13 (d, 2H, J=7.81 Hz), 6.06 (d, J=9.76 Hz, 1H), 5.85 (d, J=10.49 Hz, 1H), 2.21 (s, 3H); MS (APCI) m/z 295 [M−H]$^−$; Anal. calcd for $C_{21}H_{16}N_2$.0.15 mol $H_2O$, C, 84.34; H, 5.49; N, 9.37. Found: C, 84.03; H, 5.54; N, 9.17.

Example 6

2-[(4-Methoxyphenyl)(1-naphthyl)methyl]malononitrile

A flask was charged with (1-naphthalenylmethylene)-propanedinitrile of Example 3(408 mg, 2 mmol) and 10 mL of anhydrous tetrahydrofuran. To this stirred solution was added, at room temperature, 4-methoxyphenyl magnesium bromide (4.8 mL, 2.4 mmol, 0.5 M in tetrahydrofuran). The reaction was stirred 1.5 hours, after which it was quenched with 1 N hydrochloric acid and taken up in ethyl acetate. The organic layer was washed with saturated aqueous sodium bicarbonate, brine, dried over magnesium sulfate, filtered, and evaporated to dryness. Following purification on silica (20% ethyl acetate/hexanes) 465 mg product was isolated as an off white foam.

$^1$H NMR 400 MHz (DMSO-$d_6$): δ 8.25 (m, 1H), 7.93 (m, 1H), 7.90 (s, 1H), 7.79 (d, 1H, J=7.32 Hz), 7.61 (t, 1H, J=7.81 Hz), 7.52 (m, 2H), 7.40 (d, 2H, J=8.79 Hz), 6.88 (d, 2H, J=8.79 Hz), 6.05 (d, 1H, J=10.49 Hz), 5.84 (d, 1H, J=10.49 Hz), 3.68 (s, 3H); MS (APCI) m/z 330 [M+NH$_4$]$^+$; Anal. calcd for $C_{21}H_{16}N_2O$.0.4 mol $H_2O$: C, 78.93; H, 5.30; N, 8.77. Found: C, 79.09; H, 5.11; N, 8.47.

Example 7

2-[(2-Methoxyphenyl)(1-naphthyl)methyl]-2-methylmalononitrile

2-[(2-Methoxyphenyl)(1-naphthyl)methyl]malononitrile of Example 1 (196 mg, 0.63 mmol) was dissolved in 10 mL of tetrahydrofuran and cooled to −35° C. Potassium hexamethyldisilyl amide (1.14 mL, 0.75 mmol, 0.66 M in toluene) was added. The cooling bath was removed, and the reaction allowed to warm to room temperature, after which methyl iodide (0.078 mL, 125 mmol) was added. The reaction mixture was stirred 30 minutes, then quenched with 1 N hydrochloric acid and taken up in ethyl acetate. The organic layer was washed with saturated aqueous sodium bicarbonate, brine, dried over mgnesium sulfate, filtered, and evaporated to dryness. Following purification on silica (20% ethyl acetate/hexanes) and recrystallization from methanol, 104 mg product was isolated as a crystalline solid, mp 175-177° C.

$^1$H NMR 400 MHz (DMSO-$d_6$): δ 8.10 (m, 1H), 7.95 (m, 3H), 7.64 (t, 1H, J=7.75 Hz), 7.52 (m, 2H), 7.31 (m, 2H), 7.14 (d, 1H, J=7.57 Hz), 6.91 (td, 1H, J=7.57 Hz, 0.98 Hz), 5.93 (s, 1H), 3.91 (s, 3H), 1.90 (s, 3H)$^−$; MS (APCI) m/z 327 [M+H]$^+$;

Anal. calcd for $C_{22}H_{18}N_2O$: C, 80.96; H, 5.56; N, 8.58. Found: C, 80.91; H, 5.56; N, 8.55.

Example 8

2-[Di(1-naphthyl)methyl]malononitrile

A flask was charged with (1-naphthalenylmethylene)-propanedinitrile of Example 3 (408 mg, 2 mmol) and 10 mL anhydrous tetrahydrofuran. To this stirred solution was added, at room temperature, 1-naphthyl-magnesium bromide (12.5 mL, 2.5 mmol, 0.1 M in tetrahydrofuran). The reaction was stirred 2 hours, after which it was quenched with 1 N hydrochloric acid and taken up in ethyl acetate. The organic layer was washed with saturated aqueous sodium bicarbonate, brine, dried over magnesium sulfate, filtered, and evaporated to dryness. The residue was recrystallized from ethanol to yield 231 mg product as a crystalline solid, mp 179-181° C.

$^1$H NMR 400 MHz (DMSO-d$_6$): δ 8.41 (m, 2H), 7.96 (m, 2H), 7.91 (d, 2H, J=8.05 Hz), 7.60 (dd, 2H, J=7.32 Hz, 0.98 Hz), 7.53 (m 6H), 6.76 (d, 1H, J=9.52 Hz), 6.08 (d, 1H, J=9.27 Hz); MS (APCI) m/z 331 [M−H]$^−$; Anal. calcd for $C_{24}H_{16}N_2$: C, 86.72; H, 4.85; N, 8.43. Found: C, 86.53; H, 4.70; N, 8.51.

Example 9

2-(2-Fluoro-benzylidene)-malononitrile

Malononitrile (3.303 g, 50 mmol), 2-fluorobenzaldehyde (6.205 g, 50 mmol), 1 g of molecular sieves, and 500 mg of a resin bound piperidine (described in *Tetrahedron Lett.*, 1999, 40, 7031-33) were placed in a vessel which was irradiated in a 300 W single mode microwave for 15 seconds. The reaction mixture was taken up in iso-propyl acetate, filtered, evaporated, taken up in dichloromethane, filtered through a pad of Magnasol, evaporated, and recrystallized from ethanol to yield 2.435 g of the title material as a crystalline solid, mp 117-118° C. (*Can. J. Chem.*, 1967, 45 1001-06)
$^1$H NMR 400 MHz (DMSO-d$_6$): δ 8.58 (s, 1H), 8.04 (td, 1H, J=7.57 Hz, 1.71 Hz), 7.74 (m, 1H), 7.45 (m, 2H); MS (APCI) m/z 172 (M)$^−$; Anal. calcd for $C_{10}H_5FN_2$: C, 69.77; H, 2.93 N, 16.27. Found: C, 69.65; H, 2.67 N, 16.33.

Example 10

In Vitro Methods

Cells

T-175 flasks of 100% confluent HAECT-1 cells (immortalized human aortic endothelial cells) were washed with 8 ml of HBSS (HEPES buffered saline solution) and infected for four hours with 6 ml of a 1:10 dilution of Ad5-wt-hERα virus (an adenovirus transfection vector that mediates CMV promoter driven expression of human ERα) in phenol red free Endothelial Cell Basal medium (Clonetics, San Diego Calif., Catalog # CC-3129) containing 0.25% bovine serum albumin (EBM-BSA). After four hours, cells were washed with EBM-BSA and incubated overnight in the same medium. Following overnight incubation, cells were washed with EBM-BSA and infected for 2 hours with 6 ml of a 1:10 dilution of Ad5-3× (NFκB).Luc virus (Adenovirus luciferase expression vector driven by 3 repeats of the MHC NFκβ site 5' to the thymidine kinase promoter) in EBM-BSA. After two hours, cells were washed and incubated at 34° C. for 1 hour. Cells were then washed, trypsinized, counted and resuspended in 95% FBS/5% dimethylsulfoxide at a concentration of 4×10$^6$ cells/ml, frozen as 1 or 5 ml aliquots in cryo-vials and stored at −150° C. Control (no ER infection) cells were processed as above without Ad5-wt-hERα virus infection.

IL-6 and Creatine Kinase Assays

ERα infected HAECT-1 cells or control cells were thawed, diluted 42× in warm EBM-BSA, plated into 96-well plates at 0.1 ml/well and incubated for 4 h at 34° C. Test compounds were added to the cells as 2× stocks in EBM-BSA containing 2 ng/ml IL-1β (R&D Systems) and plates were returned to the incubator (34° C.). After 15-20 h, 100 μl aliquots of media were removed from the cells and assayed for IL-6 content using a BioSource human IL-6 ELISA Kit. Cells were subsequently washed with 300 μl of Dulbecco's phosphate buffered saline and lysed in 50 μl of Cell Culture Lysis Reagent (Promega). Luciferase was determined on a Wallac Victor$^2$ Luminometer (Gaithersburg, Md.) using 10 μl of lysate and mixing with 100 μl of Promega Luciferase Assay reagent. Creatine kinase was determined from the rate of increase in $A_{340}$ following addition of 100 μl of CK assay reagent (Sigma, cat. No 47-10) to the remainder of the cell lysate.

Data Analyses

For IC$_{50}$ and EC$_{50}$ calculations, mean IL-6, luciferase or CK values versus log$_{10}$ of the compound concentration were fitted to a four parameter logistic equation. The IC$_{50}$/EC$_{50}$ value, 'Hill slope', upper and lower limits of the curve were iteratively estimated.

Mice

Ovariectomized C57BL/6 mice (16-20 g) (Taconic) were separated into groups of 8. After 5-7 days of recuperation, the mice were fed a chow diet or an atherogenic diet (15.75% fat, 1.25% cholesterol and 0.5% sodium cholate) (Purina diet #21539). EE or test compound was administered once daily by gavage in a methylcellulose/tween vehicle (0.1 ml per mouse) for 5 weeks. At the end of the experimental period, the liver was collected and uterine wet weight was recorded.

RNA Analysis

Liver total RNA was prepared by using Trizol reagent (BRL). Estrogen and compound regulation of NF-κB target genes were verified by real time RT-PCR using an ABI PRISM 7700 Sequence Detection System according to the manufacturer's protocol (Applied Biosystems). The data was analyzed using the Sequence Detector v1.7 software (Applied Biosystems) and normalized to GAPDH using the Applied Biosystems primer set.

In Vitro Results

Table 1 summarizes the activities of E2 and several "anti-inflammatory estrogens" in the HAECT-1 NF-κB, IL-6 and creatine kinase assays in Ad5-wt-ER infected cells. Table 2 lists the activities of the same compounds in the HAECT-1 NF-κB and creatine kinase assays in uninfected cells.

TABLE 1

Effects of 17-β-estradiol on NF-κB, IL-6 and CK expression in Ad5-wt-ER infected HAECT-1 cells

| | NF-κB | | IL-6 | | CK | |
|---|---|---|---|---|---|---|
| Compound | IC$_{50}$ (nM) | Efficacy (%) | IC$_{50}$ (nM) | Efficacy (%) | IC$_{50}$ (nM) | Efficacy (%) |
| E2 | 1 | 100 | 1.7 | 100 | 5.8 | 100 |
| Ex. 1 | 29 | 104 | 1218 | 118 | 8.7 | 27 |
| | 312 | 126 | | | | |
| Ex. 3 | 853 | 138 | 1044 | 92 | inactive | |
| Ex. 4 | 158 | 101 | 1011 | 127 | inactive | |

TABLE 1-continued

Effects of 17-β-estradiol on NF-κB, IL-6 and
CK expression in Ad5-wt-ER infected HAECT-1 cells

| Com-pound | NF-κB | | IL-6 | | CK | |
|---|---|---|---|---|---|---|
| | $IC_{50}$ (nM) | Efficacy (%) | $IC_{50}$ (nM) | Efficacy (%) | $IC_{50}$ (nM) | Efficacy (%) |
| | 674 | 147 | | | | |
| Ex. 5 | 1661 | 154 | | | inactive | |
| Ex. 6 | 1644 | 137 | | | | |
| Ex. 7 | 9.9 | 98 | 24 | 144 | 30.7 | 28 |
| | 17.5 | 89 | | | | |
| Ex. 8 | 768 | 176 | 560 | 152 | | |
| | 581 | 179 | | | | |

*Efficacy values are relative to the maximal inhibition (NF-κB or IL-6 assay) or stimulation (CK assay) observed with E2

TABLE 2

Effects of 17-β-estradiol on NF-κB and
CK expression in non ER infected HAECT-1 cells

| | NF-κB | | CK | |
|---|---|---|---|---|
| Compound | $IC_{50}$ (nM) | Efficacy (%) | $IC_{50}$ (nM) | Efficacy (%) |
| E2 | inactive | | inactive | |
| Ex. 1 | inactive | | inactive | |
| Ex. 7 | inactive | | inactive | |

E2 inhibits NF-κB and IL-6 expression in Ad5-wt-ER infected HAECT-1 cells with an $IC_{50}$ value around 1 nM and induces expression of creatine kinase in the same cells with similar potency (5.8 nM) (Table 1). In contrast, the compounds of the instant invention inhibit NF-κB and IL-6 expression in Ad5-wt-ER infected HAECT-1 cells show reduced or no CK expression (Table 1). The above compounds inhibit NF-κB expression in an ER-dependent manner as indicated by their inactivity on IL6 in HAECT-1 cells not infected with the Ad5-wt-ER virus (Table 2). The ability of the instant compounds to inhibit NF-κB and IL-6 expression without inducing CK activity (Table 1) is consistent with an anti-inflammatory activity in the absence of classic estrogenic activity.

Example 12

In Vivo Activity

To determine the ability of estrogens to regulate the development of diet-induced inflammation in the liver, gene expression changes resulting from the atherogenic diet were monitored. Ovariectomized C57BL/6 mice were fed either a chow or atherogenic diet and treated daily with EE (0.01 mg/kg) or test compound (10 mg/kg) (Table 3). Real time RT-PCR analysis confirmed the atherogenic diet induction of mRNA for MHC invariant chain (MHI), VCAM-1, RANTES, and TNF-α and treatment with EE strongly suppressed the induction of these genes.

Treatment with the test compound did not result in a significant induction in uterine wet weight increase, an undesirable activity associated with EE (Table 3).

TABLE 3

Effects of EE (0.01 mg/kg/day) and test compound
(10 mg/kg/day) on uterine wet weight increase
in C57BL/6 compared to vehicle control.

| | Uterine Wet Weight Increase | |
|---|---|---|
| Compound | Fold Increase | Efficacy (%) |
| EE | 5.0 | 100 |
| Ex. 7 | 2.2 | 18 |

Evaluation of Test Compounds Using an ERE-Reporter Test Procedure in MCF-7 Breast Cancer Cells Stock solutions of test compounds (usually 0.1 M) are prepared in DMSO and then diluted 10 to 100-fold with DMSO to make working solutions of 1 or 10 mM. The DMSO stocks are stored at either 4° C. (0.1 M) or −20° C. (<0.1 M). MCF-7 cells are passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000 cells/well into 96 well plates and incubated at 37° C. overnight.

The cells are infected for 2 hr at 37° C. with 50 μl/well of a 1:10 dilution of adenovirus 5-ERE-tk-luciferase in experimental medium [phenol red-free D-MEM/F-12 medium containing 10% (v/v) heat-inactivated charcoal-stripped fetal bovine serum, 1% (v/v) Penicillin-Streptomycin, 2 mM glutaMax-1, 1 mM sodium pyruvate]. The wells are then washed once with 150 μl of experimental medium. Finally, the cells are treated for 24 hr at 37° C. in replicates of 8 wells/treatment with 150 μl/well of vehicle (≦0.1% v/v DMSO) or compound that is diluted ≧1000-fold into experimental medium.

Initial screening of test compounds is done at a single dose of 1 μM that is tested alone (estrogen receptor agonist mode) or in combination with 0.1 nM 17β-estradiol ($EC_{80}$; estrogen receptor antagonist mode). Each 96 well plate also includes a vehicle control group (0.1% v/v DMSO) and an estrogen receptor agonist control group (either 0.1 or 1 nM 17β-estradiol). Dose-response experiments are performed in either the estrogen receptor agonist and/or estrogen receptor antagonist modes on active compounds in log increases from $10^{-14}$ to $10^{-5}$ M. From these dose-response curves, $EC_{50}$ and $IC_{50}$ values, respectively, are generated. The final well in each treatment group contains 5 μl of $3\times10^{-5}$ M ICI-182,780 ($10^{-6}$ M final concentration) as an estrogen receptor antagonist control.

After treatment, the cells are lysed on a shaker for 15 min with 25 μl/well of 1× cell culture lysis reagent (Promega Corporation). The cell lysates (20 μl) are transferred to a 96 well luminometer plate, and luciferase activity is measured in a MicroLumat LB 96 P luminometer (EG & G Berthold) using 100 μl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS Institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the estrogen receptor agonist mode, or the positive estrogen receptor agonist control results (0.1 nM 17β-estradiol) in the estrogen receptor antagonist mode. For the initial single dose experiment, if the compound treatment results are significantly different from the appropriate control ($p<0.05$), then the results are reported as the percent relative to the 17β-estradiol control [i.e., ((compound−vehicle control)/(17β−estradiol control−vehicle control))× 100]. The JMP software is also used to determine the $EC_{50}$ and/or $IC_{50}$ values from the non-linear dose-response curves.

Evaluation of Uterotrophic Activity

Uterotrophic activity of a test compound can be measured according to the following standard pharmacological test procedures.

Procedure 1: Sexually immature (18 days of age) Sprague-Dawley rats are obtained from Taconic and provided unrestricted access to a casein-based diet (Purina Mills 5K96C) and water. On day 19, 20 and 21 the rats are dosed subcutaneously with 17α-ethinyl-17β-estradiol (0.06 µg/rat/day), test compound or vehicle (50% DMSO/50% Dulbecco's PBS). To assess estrogen receptor antagonist, compounds are coadministered with 17α-ethinyl-17β-estradiol (0.06 µg/rat/day). There are six rats/group and they are euthanized approximately 24 hours after the last injection by $CO_2$ asphyxiation and pneumothorax. Uteri are removed and weighed after trimming associated fat and expressing any internal fluid. A tissue sample can also be snap frozen for analysis of gene expression (e.g. complement factor 3 mRNA).

Procedure 2: Sexually immature (18 days of age) 129 SvE mice are obtained from Taconic and provided unrestricted access to a casein-based diet (Purina Mills 5K96C) and water. On day 22, 23, 24 and 25 the mice are dosed subcutaneously with compound or vehicle (corn oil). There are six mice/group and they are euthanized approximately 6 hours after the last injection by $CO_2$ asphyxiation and pneumothorax. Uteri are removed and weighed after trimming associated fat and expressing any internal fluid.

Evaluation of Osteoporosis and Livid Modulation (Cardioprotection)

Female Sprague-Dawley rats, ovariectomized or sham operated, are obtained 1 day after surgery from Taconic Farms (weight range 240-275 g). They are housed 3 or 4 rats/cage in a room on a 12/12 (light/dark) schedule and provided with food (Purina 5K96C rat chow) and water ad libitum. Treatment for all studies begin 1 day after arrival and rats are dosed 7 days per week as indicated for 6 weeks. A group of age matched sham operated rats not receiving any treatment serve as an intact, estrogen replete control group for each study.

All test compounds are prepared in a vehicle of 50% DMSO (JT Baker, Phillipsburg, N.J.)/1× Dulbecco's phosphate saline (GibcoBRL, Grand Island, N.Y.) at defined concentrations so that the treatment volume is 0.1 mL/100 g body weight. 17β-estradiol is dissolved in corn oil (20 µg/mL) and delivered subcutaneously, 0.1 mL/rat. All dosages are adjusted at three week intervals according to group mean body weight measurements, and given subcutaneously.

Five weeks after the initiation of treatment and one week prior to the termination of the study, each rat is evaluated for bone mineral density (BMD). The total and trabecular density of the proximal tibia are evaluated in anesthetized rats using an XCT-960M (PQCT; Stratec Medizintechnik, Pforzheim, Germany). The measurements are performed as follows: Fifteen minutes prior to scanning, each rat is anesthetized with an intrapentoneal injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 90° angle and the knee joint at 180°. The polycarbonate tube is affixed to a sliding platform that maintains it perpendicular to the aperture of the pQCT. The platform is adjusted so that the distal end of the femur and the proximal end of the tibia is in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is mathematically removed using an iterative algorithm. The density of the remaining bone (total density) is reported in $mg/cm^3$. The outer 55% of the bone is mathematically peeled away in a concentric spiral. The density of the remaining bone (Trabecular density) is reported in $mg/cm^3$ One week after BMD evaluation the rats are euthanized by $CO_2$ asphyxiation and pneumothorax, and blood is collected for cholesterol determination. The uteri are also removed and the weighed after trimming associated fat and expressing any luminal fluid. Total cholesterol is determined using a Boehringer-Mannheim Hitachi 911 clinical analyzer using the Cholesterol/HP kit. Statistics were compared using one-way analysis of variance with Dunnet's test.

Evaluation of Antioxidant Activity

Porcine aortas are obtained from an abattoir, washed, transported in chilled PBS, and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15-20 minutes, after which the collagenase solution is collected and centrifuged for 5 minutes at 2000×g. Each pellet is suspended in 7 mL of endothelial cell culture medium consisting of phenol red free DMEM/Ham's F12 media supplemented with charcoal stripped FBS (5%), NuSerum (5%), L-glutamine (4 mM), penicillin-streptomycin (1000 U/ml, 100 µg/ml) and gentamycin (75 µg/ml), seeded in 100 mm petri dish and incubated at 37° C. in 5% $CO_2$. After 20 minutes, the cells are rinsed with PBS and fresh medium added, this was repeated again at 24 hours. The cells are confluent after approximately 1 week. The endothelial cells are routinely fed twice a week and, when confluent, trypsinized and seeded at a 1:7 ratio. Cell mediated oxidation of 12.5 µg/mL LDL is allowed to proceed in the presence of the compound to be evaluated (5 µM) for 4 hours at 37° C. Results are expressed as the percent inhibition of the oxidative process as measured by the TBARS (thiobarbituric acid reactive substances) method for analysis of free aldehydes [Yagi, *Biochemical Medicine*, 1976, 15, 212-6].

Progesterone Receptor mRNA Regulation Standard Pharmacological Test Procedure

This test procedure can be used to evaluate the estrogenic or antiestrogenic activity of compounds from this invention [Shughrue et al., *Endocrinology*, 1997, 138, 5476-5484].

Rat Hot Flush Test Procedure

The effect of test compounds on hot flushes can be evaluated in a standard pharmacological test procedure which measures the ability of a test compound to blunt the increase in tail skin temperature which occurs as morphine-addicted rats are acutely withdrawn from the drug using naloxone [Merchenthaler et al., *Maturitas*, 1998 30, 307-16]. It can also be used to detect estrogen receptor antagonist activity by co-dosing test compound with the reference estrogen.

Evaluation of Vasomotor Function in Isolated Rat Aortic Rings

Sprague-Dawley rats (240-260 grams) are divided into 4 groups:
1. Normal non-ovariectomized (intact)
2. Ovariectomized (ovex) vehicle treated
3. Ovariectomized 17β-estradiol treated (1 mg/kg/day)
4. Ovariectomized animals treated with test compound (various doses)

Animals are ovariectomized approximately 3 weeks prior to treatment. Each animal receives either 17-β estradiol sulfate (1 mg/kg/day) or test compound suspended in distilled, deionized water with 1% tween-80 by gastric gavage. Vehicle treated animals received an appropriate volume of the vehicle used in the drug treated groups.

Animals are euthanized by $CO_2$ inhalation and exsanguination. Thoracic aortae are rapidly removed and placed in 37° C. physiological solution with the following composition (mM): NaCl (54.7), KCl (5.0), $NaHCO_3$ (25.0), $MgCl_2$, $2H_2O$ (2.5), D-glucose (11.8) and $CaCl_2$ (0.2) gassed with $CO_2$—$O_2$, 95%/5% for a final pH of 7.4. The advantitia is removed from the outer surface and the vessel is cut into 2-3 mm wide rings. Rings are suspended in a 10 mL tissue bath with one end attached to the bottom of the bath and the other to a force transducer. A resting tension of 1 gram is placed on the rings. Rings are equilibrated for 1 hour, signals are acquired and analyzed.

After equilibration, the rings are exposed to increasing concentrations of phenylephrine ($10^{-8}$ to $10^{-4}$ M) and the tension recorded. Baths are then rinsed 3 times with fresh buffer. After washout, 200 mM L-NAME is added to the tissue bath and equilibrated for 30 minutes. The phenylephrine concentration response curve is then repeated.

Evaluation of Cardioprotective Activity

Apolipoprotein E-deficient C57/B1J (apo E KO) mice are obtained from Taconic Farms. All animal procedures are performed under strict compliance to IACUC guidelines. Ovariectomized female apo E KO mice, 4-7 weeks of age, are housed in shoe-box cages and were allowed free access to food and water. The animals are randomized by weight into groups (n=12-15 mice per group). The animals are dosed with test compounds or estrogen (17β-estradiol sulfate at 1 mg/kg/day) in the diet using a Precise-dosing Protocol, where the amount of diet consumed is measured weekly, and the dose adjusted accordingly, based on animal weight. The diet used is a Western-style diet (57U5) that is prepared by Purina and contains 0.50% cholesterol, 20% lard and 25 IU/KG Vitamin E. The animals are dosed/fed using this paradigm for a period of 12 weeks. Control animals are fed the Western-style diet and receive no compound. At the end of the study period, the animals are euthanized and plasma samples obtained. The hearts are perfused in situ, first with saline and then with neutral buffered 10% formalin solution.

For the determination of plasma lipids and lipoproteins, total cholesterol and triglycerides are determined using enzymatic methods with commercially available kits from Boehringer Mannheim and Wako Biochemicals, respectively and analyzed using the Boehringer Mannheim Hitachii 911 Analyzer. Separation and quantification of plasma lipoproteins were performed using FPLC size fractionation. Briefly, 50-100 mL of serum is filtered and injected into Superose 12 and Superose 6 columns connected in series and eluted at a constant flow rate with 1 mM sodium EDTA and 0.15 M NaCl. Areas of each curve representing VLDL, LDL and HDL are integrated using Waters Millennium™ software, and each lipoprotein fraction is quantified by multiplying the Total Cholesterol value by the relative percent area of each respective chromatogram peak.

For the quantification of aortic atherosclerosis, the aortas are carefully isolated and placed in formalin fixative for 48-72 hours before handling. Atherosclerotic lesions are identified using Oil Red O staining. The vessels are briefly destained, and then imaged using a Nikon SMU800 microscope fitted with a Sony 3CCD video camera system in concert with IMAQ Configuration Utility (National Instrument) as the image capturing software. The lesions are quantified en face along the aortic arch using a custom threshold utility software package (Coleman Technologies). Automated lesion assessment is performed on the vessels using the threshold function of the program, specifically on the region contained within the aortic arch from the proximal edge of the brachio-cephalic trunk to the distal edge of the left subclavian artery. Aortic atherosclerosis data are expressed as percent lesion involvement strictly within this defined luminal area.

Evaluation of Cognition Enhancement

Ovariectomized rats (n=50) are habituated to an 8-arm radial arm maze for 10-min periods on each of 5 consecutive days. Animals are water-deprived prior to habituation and testing. A 100 μL aliquot of water placed at the ends of each arm serves as reinforcement. Acquisition of a win-shift task in the radial arm maze is accomplished by allowing the animal to have access to one baited arm. After drinking, the animal exits the arm and re-enters the central compartment, where it now has access to the previously visited arm or to a novel arm. A correct response is recorded when the animal chooses to enter a novel arm. Each animal is given 5 trials per day for 3 days. After the last acquisition trial, the animals are assigned to one of the following 4 groups:
1. Negative controls: injected with 10% DMSO/sesame oil vehicle once daily for 6 days (1 mL/kg, SC)
2. Positive controls: injected with 17β-estradiol benzoate for 2 day and tested 4 days after the second injection (17β-estradiol benzoate at 10 μg/0.1 mL per rat)
3. Estradiol: 17β-estradiol will be injected daily for 6 days (20 μg/kg, SC)
4. Test compound: injected daily for 6 days (doses vary).

All injections will begin after testing on the last day of acquisition. The last injection for groups 1, 3, and 4 will take place 2 hours before testing for working memory.

The test for working memory is a delayed non-matching-to-sample task (DNMS) utilizing delays of 15, 30, or 60 seconds. This task is a variation of the acquisition task in which the rat is placed in the central arena and allowed to enter one arm as before. A second arm is opened once the rat traverses halfway down the first arm, and again the rat is required to choose this arm. When it has traveled halfway down this second arm, both doors are closed and the delay is instituted. Once the delay has expired, both of the original two doors, and a third novel door, are opened simultaneously. A correct response is recorded when the animal travels halfway down the third, novel arm. An incorrect response is recorded when the animal travels halfway down either the first or second arms. Each animal will receive 5 trials at each of the three delay intervals for a total of 15 trials per subject.

Evaluation of Effect on Pleurisy

The ability to reduce the symptoms of experimentally-induced pleurisy in rats can be evaluated according to the procedure of Cuzzocrea [*Endocrinology* 141: 1455-63 (2000)].

Evaluation of Protection Against Glutamate-Induced Cytotoxicity (Neuroprotection)

The neuroprotective activity of compounds of this invention can be evaluated in an in vitro standard pharmacological test procedure using glutamate challenge [Zaulyanov et al., *Cellular & Molecular Neurobiology*, 1999, 19, 705-18; Prokai et al., *Journal of Medicinial Chemistry*, 2001, 44, 110-4].

Evaluation in the Mammary End Bud Test Procedure

Estrogens are required for full ductal elongation and branching of the mammary ducts, and the subsequent development of lobulo-alveolar end buds under the influence of progesterone. In this test procedure, the mammotrophic activity of selected compounds of the invention can be evaluated according to the following standard pharmacological test procedure. Twenty-eight day old Sprague-Dawley rats (Taconic Farms, Germantown, N.Y.) are ovariectomized and rested for nine days. Animals are housed under a 12-hour light/dark cycle, fed a casein-based Purina Laboratory Rodent Diet 5K96 (Purina, Richmond, Ind.) and allowed free access to water. Rats were then dosed subcutaneously for six days with vehicle (50% DMSO (JT Baker, Phillipsburg, N.J.)/50% 1× Dulbecco's Phosphate buffered saline (GibcoBRL, Grand Island, N.Y.), 17β-estradiol (0.1 mg/kg) or test compound (20 mg/kg). For the final three days, rats are also dosed subcutaneously with progesterone (30 mg/kg). On the seventh day, rats are euthanised and a mammary fat pad excised. This fat pad is analyzed for casein kinase II mRNA as a marker of end bud proliferation. Casein kinase II mRNA is anlayzed by real-time RT-PCR. Briefly, RNA is isolated following Trizol (GibcoBRL, Grand Island, N.Y.) according to the manufacture's directions, Samples are treated with DNAse I using DNA-free kit (Ambion), and casein kinase II mRNA levels are measured by real-time RT-PCR using the Taqman Gold procedure (PE Applied Biosystems). A total of 50 ng of RNA is analyzed in triplicate using casein kinase II specific primer pair (5' primer, CACACGGATGGCGCATACT, SEQ ID NO: 1; 3' primer, CTCGGGATGCACCATGAAG, SEQ ID NO: 2) and customized probe (TAMRA-CGGCACTGGTTTCCCT-CACATGCT-FAM, SEQ ID NO: 3). Casein kinase II mRNA levels are normalized to 18s ribosomal RNA contained within each sample reaction using primers and probe supplied by PE Applied Biosystems.

Evaluation in the HLA Rat Standard Pharmacological Test Procedure for Inflammatory Bowel Disease Representative compounds can be evaluated in the HLA rat standard pharmacological test procedure which emulates inflammatory bowel disease in humans. The following briefly describes the procedure used and results obtained. Male HLA-B27 rats are obtained from Taconic and provided unrestricted access to food (PMI Lab diet 5001) and water. Rats are dosed subcutaneously once per day with either vehicle (50% DMSO/50% 1× Dulbecco's Phosphate Buffered Saline) or test compound (0.1 to 10 mg/kg) for at least one week. Stool quality is observed daily and graded according to the following scale: Diarrhea=3; soft stool=2; normal stool=1. At the end of the study, serum is collected and stored at −70° C. A section of colon is prepared for histological analysis and an additional segment is analyzed for myeloperoxidase activity.

For histological analysis, colonic tissue is immersed in 10% neutral buffered formalin. Each specimen of colon is separated into four samples for evaluation. The formalin-fixed tissues are processed in a Tissue Tek vacuum infiltration processor (Miles, Inc; West Haven, Conn.) for paraffin embedding. The samples are sectioned at 5 µm and then stained with hematoxylin and eosin (H&E) for blinded histologic evaluations using a scale modified after Boughton-Smith. After the scores are completed the samples are unblinded, and data are tabulated and analyzed by ANOVA linear modeling with multiple mean comparisons. Sections of colonic tissue are evaluated for several disease indicators and given relative scores.

Evaluation in Three Models of Arthritis

Lewis rat assay of adjuvant-induced arthritis. Sixty, female, 12 weeks old, Lewis rats are housed according to standard facility operating procedures. They receive a standard regimen of food and water ad libitum. Each animal is identified by a cage card indicating the project group and animal number. Each rat number is marked by indelible ink marker on the tail. At least 10-21 days before study they are anesthetized and ovariectomized by standard aseptic surgical techniques.

Freund's Adjuvant-Complete (Sigma Immuno Chemicals, St. Louis, Mo.) is used to induce arthritis, each mL containing 1 mg *Mycobacterium tuberculosis* heat killed and dried, 0.85 mL mineral oil and 0.15 mL mannide monooleate Lot No. 084H8800.

The following are examples of two test procedures. Inhibition test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (JT Baker, Phillipsburg, N.J.)/1× Dulbecco's phosphate saline (GibcoBRL, Grand Island, N.Y.)) or test compound (0.1-10 mg/kg, administered subcutaneously). All rats begin treatment on Day 1.

Treatment test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (JT Baker, Phillipsburg, N.J.)/1× Dulbecco's phosphate saline (GibcoBRL, Grand Island, N.Y.)) or test compound (0.1-10 mg/kg, administered subcutaneously). All rats begin treatment on Day 8 after adjuvant injection.

Statistical analysis is performed using Abacus Concepts SuperANOVA. (Abacus Concepts, Inc., Berkeley, Calif.). All of the parameters of interest are subjected to Analysis of Variance with Duncan's new multiple range post hoc testing between groups. Data are expressed throughout as mean ±standard deviation (SD), and differences are deemed significant if $p<0.05$.

The degree of arthritis severity is monitored daily in terms of the following disease indices: Hindpaw erythema, hindpaw swelling, tenderness of the joints, and movements and posture. An integer scale of 0 to 3 is used to quantify the level of erythema (0=normal paw, 1=mild erythema, 2=moderate erythema, 3=severe erythema) and swelling (0=normal paw, 1=mild swelling, 2=moderate swelling, 3=severe swelling of the hind paw). The maximal score per day is 12.

At the end of the study the rats are euthanized with $CO_2$, hindlimbs removed at necropsy and fixed in 10% buffered formalin, and the tarsal joints decalcified and embedded in paraffin. Histologic sections are stained with Hematoxylin and Eosin or Saffranin O—Fast Green stain.

Slides are coded so that the examiner is blinded to the treatment groups. Synovial tissue from tarsal joints is evaluated based on synovial hyperplasia, inflammatory cell infiltration, and pannus formation [Poole and Coombs, *International Archives of Allergy & Applied Immunology*, 1997, 54, 97-113] as outlined below.

| Category | Grade |
|---|---|
| 1. Synovial lining cells | |
| a. No change | 0 |
| b. Cells enlarged, slightly thickened | 1 |
| c. Cells enlarged, increase in numbers, moderately thickened. No villus present | 2 |
| d. Cells enlarged, thickened. Villlus present | 3 |
| 2. Fibroplasia | |
| a. No change | 0 |
| b. Fibroplasia present under lining cells | 1 |
| c. Small areas of areolar tissue replaced by fibrous tissue | 2 |
| d. Replacement of areolar tissue by fibrous tissue | 3 |
| 3. Inflammatory cells | |
| a. Occasionally seen, scattered throughout selection | 0 |
| b. Cells present in small numbers in or just under lining cell layer and/or around blood vessels. | 1 |
| c. Small focal collection of cells may be present | 2 |
| d. Large numbers of cells present in capsule and in or under lining cell layers. Large foci often seen. | 3 |
| 4. Pannus | |
| a. Not detectable | 0 |
| b. Detectable | 1 |

In addition, articular cartilage and bone is evaluated using Mankin's histological grading system [Mankin et al., *Journal of Bone & Joint Surgery—American Volume*, 1971, 53, 523-37] as shown below.

| Category | Grade |
|---|---|
| 1. Structure | |
| a. Normal | 0 |
| b. Surface irregularity | 1 |
| c. Pannus and surface irregularity | 2 |
| d. Clefts to transitional zone | 3 |
| e. Clefts to radial zone | 4 |
| f. Clefts to calcified zone | 5 |
| g. Complete disorganization | 6 |
| 2. Cells | |
| a. Normal | 0 |
| b. Diffuse hypercellularity | 1 |
| c. Cloning | 2 |
| d. Hypocellularity | 3 |
| 3. Safranin-O staining | |
| a. Normal | 0 |
| b. Slight reduction | 1 |
| c. Modest reduction | 2 |
| d. Severe reduction | 3 |
| e. No dye noted | 4 |
| 4. Tidemark integrity | |
| a. Intact | 0 |
| b. Crossed by blood vessels | 1 |

Evaluation in the HLA-B27 Rat Model of Arthritis.

Representative compounds are evaluated in the HLA-B27 rat standard pharmacological test procedure which emulates arthritis in humans. The following briefly describes the procedure used. Male HLA-B27 rats are obtained from Taconic and provided unrestricted access to a food (PMI Lab diet 5001) and water. Rats are dosed subcutaneously once per day with either vehicle (50% DMSO/50% 1× Dulbecco's Phosphate Buffered Saline) or test compound (0.1 to 10 mg/kg) for at least one week. Joint scores and histology are evaluated as described above for the Lewis rat model of adjuvant-induced arthritis.

Evaluation in the Collagen Induced Arthritis Models.

Compounds are evaluated in BALB/c mice, 6-8 weeks of age, in which arthritis is induced by monoclonal antibodies raised against type II collagen, plus lipopolysaccharide (LPS). The animals were administered intravenously with a combination of 4 different mAbs totalling 4 mg/mouse on day 0, and followed by intravenous 25 μg of LPS 72 hours later (day 3). From day 3, one hour after LPS application, tested compounds are give orally once daily for 15 days. For each animal, increase in volume of both hind paws is measured using a plethysmometer with water cell (12 mm diameter) on days 0, 5, 7, 10, 14 and 17. Percent inhibition of increase in volume is calculated.

Evaluation in In Vivo Models of Carcinogeneisis

The ability of compounds of this invention to treat and inhibit various malignancies or hyperprolific disorders can be evaluated in standard pharmacological test procedures that are readily available in the literature, and include the following two procedures.

Breast cancer. Athymic nu/nu (nude) mice are obtained ovariectomized from Charles River Laboratories (Wilmington, Mass.). One day prior to tumor cell injection, animals are implanted with time-release pellets containing 0.36-1.7 mg 17β-estradiol (60 or 90 day release, Innovative Research of America, Sarasota, Fla.) or a placebo. The pellet is introduced subcutaneously into the intrascapular region using a 10-gauge precision trochar. Subsequently, mice are injected subcutaneously into the breast tissue with either $1 \times 10^7$ MCF-7 cells or $1 \times 10^7$ BG-1 cells. The cells are mixed with an equal volume of matrigel, a basement membrane matrix preparation to enhance tumor establishment. Test compounds can be evaluated either by dosing one day after tumor cell implantation (inhibition regimen) or after tumors have reached a certain size (treatment regimen). Compounds are administered either intraperitoneally or orally in a vehicle of 1% tween-80 in saline each day. Tumor size is evaluated every three or seven days.

Colon cancer. The ability to treat or inhibit colon cancer can be evaluated in the test procedure of Smirnoff [*Oncology Research*, 1999, 11, 255-64].

Evaluation of Neuroprotection in Two In Vivo Test Procedures

Transient global ischemia in the Mongolian gerbil. The effect of test compounds on preventing or treating brain injury in response to oxygen deprivation/reperfusion can be measured using the following test procedure.

Female Mongolian gerbils (60-80 g; Charles River Laboratories, Kingston, N.Y.) are housed in the Wyeth-Ayerst animal care facility (AAALAC certified) with a 12-hour light, 12-hour dark photoperiod and free access to tap water and a low-estrogen casein diet (Purina; Richmond, Ind.). After acclimation (3-5 days), gerbils are anesthetized with isoflurane (2-3% mixture with $O_2$), ovariectomized (Day 0). Beginning the following morning (Day 1), gerbils are treated subcutaneously each day with either vehicle (10% ETOH/corn oil), 17β-estradiol (1 mg/kg) or an experimental compound (0.1-20 mg/kg). On Day 6, gerbils (n=4-5/group) are anesthetized with isoflurane, the common carotid arteries visualized via a mid-line neck incision and both arteries simultaneously occluded for 5 minutes with non-traumatic micro aneurysm clips. After occlusion, the clips are removed to allow cerebral reperfusion and the neck incision closed with wound clips. All animals are fasted overnight prior to the global ischemia surgery, a step that facilitates consistent ischemic injury. On Day 12, gerbils are exposed to a lethal dose of $CO_2$, and the brains frozen on dry ice and stored at $-80°$ C.

The degree of neuronal protection is evaluated by in situ hybridization analysis of neurogranin mRNA. Briefly, 20 µm coronal cryostat sections are collected on gelatin-coated slides, dried and stored at $-80°$ C. At the time of processing, the desiccated slide boxes are warmed to room temperature, the slides postfixed in 4% paraformaldehyde, treated with acetic anhydride and then delipidated and dehydrated with chloroform and ethanol. Processed section-mounted slides are then hybridized with 200 µl ($6×10^6$ DPM/slide) of an antisense or sense (control) riboprobe for Neurogranin ($^{35}$S-UTP-labeled NG-241; bases 99-340), in a 50% formamide hybridization mix and incubated overnight at 55° C. in a humidified slide chamber without coverslipping. The following morning, the slides are collected in racks, immersed in 2×SSC (0.3 M NaCl, 0.03 M sodium citrate; pH 7.0)/10 mM DTT, treated with RNase A (20 µg/ml) and washed (2×30 min) at 67° C. in 0.1×SSC to remove nonspecific label. After dehydration, the slides are opposed to BioMax (BMR-1; Kodak) X-ray film overnight.

The level of neurogranin hybridization signal is used to quantitatively assess the degree of neuronal loss in the CA1 region after injury and to evaluate the efficacy of 17β-estradiol and experimental compounds. Neurogranin mRNA is selected for these studies because it is highly expressed in the hippocampal neurons including CA1, but absent in glia and other cell types present in this brain region. Therefore, measurement of the amount of neurogranin mRNA present represents surviving neurons. Relative optical density measurements of neurogranin hybridization signal are obtained from film autoradiograms with a computer based image analysis system (C-Imaging Inc., Pittsburgh, Pa.). The results from 6 sections (40 µm apart) per animal are averaged and statistically evaluated. Numerical values are reported as the mean±SEM. One-way analysis of variance is used to test for differences in the level of neurogranin mRNA and all statements of non-difference in the results section imply that $p>0.05$.

Middle cerebral artery occlusion in mice. Neuroprotection can be evaluated according to the test procedures described by Dubal [see, Dubal et al., *Proceedings of the National Academy of Sciences of the United States of America*, 2001, 98, 1952-1957, Dubal et al., *Journal of Neuroscience*, 1999, 19, 6385-6393].

Ovulation Inhibition Standard Pharmacological Test Procedure

The test procedure is used to determine whether test compounds can inhibit or change the timing of ovulation. It can also be used to determine the number of oocytes ovulated [Lundeen et al., *J. Steroid Biochm. Mol. Biol.*, 2001, 78, 137-143].

Transplantation Rejection

To test the ability of the test compounds to prevent transplant rejection. Compounds can be tested in animal models of heart transplantation (Stetson et al., *Circulation*, 2001, 104: 676-682 or transplant atherosclerosis (Deitrich et al., *Arterioscler. Thromb. Vasc Biol.*, 2000, 20:343-352; Lou et al., *Circulation*, 1996, 94, 3355-3361.

Prevention of Restenosis

The test procedure is used to determine whether test compounds can inhibit vascular smooth muscle cell proliferation after carotid artery injury similar to what occurs after balloon angioplasty. The test compounds can be tested in animal models previously described (Karas et al., *Circ Res.*, 2001, 89, 534-539; Cerek et al., *Atherosclerosis*, 1997, 131, 59-66.

Treatment of Myocardial Infarction

Test compounds can be tested in animal models of ischemia/reperfusion to determine whether they would inhibit cell death occurring during a myocardial infarction. The compounds can be tested in models described previously (Delyani et al., *J. Mol. & Cell Cardiology*, 1996, 28, 1001-1008; Izumi et al., *J. Clin. Invest.*, 2001, 108, 203-213; Chandrasekar et al., *Circulation*, 2001, 103, 2296-2302).

Treatment for Myocarditis and Congestive Heart Failure

Test compounds can be tested in models of heart failure to determine whether compounds could be an effective therapy and improve cardiac function. Compounds can be tested in animals as described previously (Yokoseki et al., Circ. Res., 2001, 89, 1-9; Wallen et al., *Hypertension*, 2000, 36, 774-779; Toshiaki et al., *Circulation*, 2001, 104, 1094-1103).

Treatment for Diabetes

Test compounds can be tested in models of diabetes to determine their effect on reversal of obesity and diet-induced insulin resistance. Compounds can be tested in animal models as previously described (Yuan et al., *Science*, 2001, 293: 1673-1677.

Treatment for Asthma

Pulmonary Inflammation Model. Sensitize mice with OVA emulsified in alum on days 0 and 14 (ip injection). On days 28 and 29, challenge with an aerosol of OVA for 20 min (1%-5% OVA) and then on Day 30 the animals are sacrificed and harvest BAL and/or lung tissue for analysis of pulmonary inflammation.

Airway Hyperresponsiveness. This model is similar to that described above however animals are challenged on 3 consecutive days with an aerosol of OVA and airway hyperresponsiveness is measured 48 h after the last challenge. BAL can also be taken at this stage if required.

To look more directly at the effects of mast cells in conjunction with ER, may use a passive cutaneous anaphylaxis model in which IgE is injected into the ear and then 24 hours later inject DNP-HSA iv. Measure ear thickness and an early and late phase reaction. Furthermore, fix tissues in K2 and embed in Epoxy resin and cut 1 um sections. These can be stained for mast cells and quantitiate the degree of mast cell degranulation.

Based on the results obtained in the standard pharmacological test procedures, the compounds of this invention are selective anti-inflammatory compounds described herein useful for the treatment and prevention of chronic inflammatory diseases without stimulating uterine and breast cell proliferation as found with classic estrogens.

Accordingly, the compounds of this invention are useful in treating or inhibiting osteoporosis and in the inhibition of bone demineralization, which may result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushin's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatment or inhibition for osteoarthritis, hypocalcemia, hypercalcemia, Paget's disease, osteomalacia, osteohalisteresis, multiple myeloma and other forms of cancer having deleterious effects on bone tissues.

The compounds of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. The compounds of this invention are also useful in treating or inhibiting benign or malignant abnormal tissue growth including, glomerulosclerosis, prostatic hypertrophy, uterine leiomyomas, breast cancer, sclerodenna, fibromatosis, endometriosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage.

The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis, uveitis, psoriasis, multiple sclerosis, systemic lupus erythematosus and sepsis.

The compounds of this invention are also useful in treating or inhibiting ocular disorders including cataracts, uveitis, and macular degeneration and in treating skin conditions such as aging, alopecia, and acne.

The compounds of this invention are also useful in treating or inhibiting metabolic disorders such as type-II diabetes, of lipid metabolism, appetite (e.g. anorexia nervosa and bulimia).

Compounds in this invention are also useful in treating or inhibiting bleeding disorders such as hereditary hemorrhagic telangiectasia, dysfunctional uterine bleeding, and combating hemorrhagic shock.

The compounds of this invention are useful in disease states where amenorrhea is advantageous, such as leukemia, endometrial ablations, chronic renal or hepatic disease or coagulation diseases or disorders.

These results suggest an anti-inflammatory role for the test compounds in terms of their ability to block inflammatory gene expression, with the desired selectivity in activity since no induction in uterine wet weights was observed.

All patents, publications, and other documents cited herein are hereby incorporated by reference in their entirety.

What is claimed:

1. A pharmaceutical composition comprising a compound of the formula:

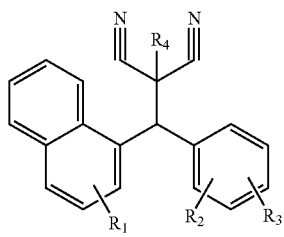

or a pharmaceutically acceptable salt, hydrate, or solvate thereof,
wherein:
$R_1$, $R_2$, and $R_3$ are each independently, hydrogen, halogen, alkyl, cycloalkyl, alkoxy, nitro, cyano, alkylthio, $CF_3$, $OCF_3$ or OH; and
$R_4$ is hydrogen, alkyl, alkenyl, arylalkyl, cycloalkyl methyl, or heteroaryl alkyl;
provided that at least one of $R_1$, $R_2$, $R_3$, and $R_4$ is other than H,
and a pharmaceutically acceptable excipient, diluent or carrier.

2. The pharmaceutical composition of claim 1 wherein $R_4$ is H.

3. The pharmaceutical composition of claim 2 wherein at least one of $R_1$, $R_2$, and $R_3$ is halogen, alkyl, cycloalkyl, alkoxy, cyano, $CF_3$, $OCF_3$ or OH.

4. The pharmaceutical composition of claim 1 wherein $R_1$ and $R_2$ are each H and $R_3$ is halogen, alkyl, alkoxy, cyano, $CF_3$ or OH.

5. The pharmaceutical composition of claim 4 wherein $R_1$ and $R_2$ are each H and $R_3$ is halogen, alkyl, or alkoxy.

6. The pharmaceutical composition of claim 5 wherein $R_4$ is H.

7. The pharmaceutical composition of claim 6 wherein $R_3$ is methyl or methoxy.

8. The pharmaceutical composition of claim 1 comprising a compound that is:
2-[(2-methoxyphenyl)(1-naphthyl)methyl]malononitrile,
2-[(3-methoxyphenyl)(1-naphthyl)methyl]malononitrile,
2-[(2-methylphenyl)(1-naphthyl)methyl]malononitrile,
2-[(4-methylphenyl)(1-naphthyl)methyl]malononitrile,
2-[(4-methoxyphenyl)(1-naphthyl)methyl]malononitrile, or
2-[(2-methoxyphenyl)(1-naphthyl)methyl]-2-methylmalononitrile.

9. The pharmaceutical composition of claim 1 wherein $R_4$ is alkyl, alkenyl, arylalkyl, cycloalkyl methyl, or heteroaryl alkyl.

10. The pharmaceutical composition of claim 1 wherein $R_1$ and $R_2$ are each, independently, hydrogen, halogen, alkyl, alkoxy, cyano, $CF_3$ or OH.

11. The pharmaceutical composition of claim 10 wherein $R_1$ and $R_2$ are the same.

12. The pharmaceutical composition of claim 10 wherein $R_3$ is hydrogen, alkyl, alkenyl, alkylaryl, or heteroaryl methyl.

13. The pharmaceutical composition of claim 10 wherein $R_1$ and $R_2$ are each, independently, hydrogen, halogen, alkyl, or alkoxy.

14. The pharmaceutical composition of claim 10 wherein $R_3$ is alkyl, allyl, or benzyl.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: Artificial sequence
<220> FEATURE:
<223> OTHER INFORMATION: primer

<400> SEQUENCE: 1
cacacggatg gcgcatact                                            19

<210> SEQ ID NO 2
<211> LENGTH: 19
<212> TYPE: DNA
<213> ORGANISM: Artificial sequence
<220> FEATURE:
<223> OTHER INFORMATION: primer

<400> SEQUENCE: 2
ctcgggatgc accatgaag                                            19

<210> SEQ ID NO 3
<211> LENGTH: 24
<212> TYPE: DNA
<213> ORGANISM: Artificial sequence
<220> FEATURE:
<223> OTHER INFORMATION: probe

<400> SEQUENCE: 3
cggcactggt ttccctcaca tgct                                      24